United States Patent [19]

McGaha et al.

[11] Patent Number: 5,650,035
[45] Date of Patent: Jul. 22, 1997

[54] COILABLE STRUCTURES CONTAINING BEADED DENTAL FLOSS AND METHODS AND APPARATUS FOR MAKING THEM

[76] Inventors: Kevin Wayne McGaha; Edward E. McCullough, both of P.O. Box 46, Brigham City, Utah 84302

[21] Appl. No.: 519,714

[22] Filed: Aug. 28, 1995

[51] Int. Cl.⁶ .................................................. B32B 31/00
[52] U.S. Cl. ........................ 156/443; 156/433; 156/434; 156/169
[58] Field of Search ........................... 156/443, 433, 156/434, 169, 173, 174, 510, 425, 430; 132/323, 324, 327

[56] References Cited

U.S. PATENT DOCUMENTS

| | | | |
|---|---|---|---|
| 4,753,254 | 6/1988 | McCullough et al. | 132/90 |
| 5,067,503 | 11/1991 | Stile | 132/324 |
| 5,167,753 | 12/1992 | McCullough et al. | |

*Primary Examiner*—James Engel
*Attorney, Agent, or Firm*—Edward E. McCullough

[57] ABSTRACT

Coilable, tape-like structures are disclosed, that contain parallel segments of dental floss. Each segment has a bead on each of its ends for handling by an applicator. The beads can be fixed to the ends of a floss segment, either by melting its ends (without allowing the melted bead to contact a solid surface) or by press fitting the floss into slits in molded beads and fixing them with a bonding agent. The coilable structures can be made, either by mounting the floss segments onto a flexible tape or by fastening beads of adjacent floss segments together. In the latter version, the floss is (optionally) made stiff enough to support its weight, laterally. Apparatus for producing the coilable structures includes an elongated, substantially-flat, rotating chassis on which floss from a tensioning dispenser is wound. In one embodiment, a tape is held onto the upper surface of the chassis while the floss is wound into slits in the edges of the tape. The floss is then divided into segments by knives on a long blade that slides in the underside of the chassis. Then the free ends of the floss are melted, to produce spheroidal beads thereon, as the tape and central portions of the segments are shielded from the heat source. When the shields are withdrawn, the floss-loaded tape is rolled into a coil. Apparatus for making coilable structures wherein beads on adjacent floss segments are fastened directly together, without a supporting tape, is also disclosed.

27 Claims, 3 Drawing Sheets

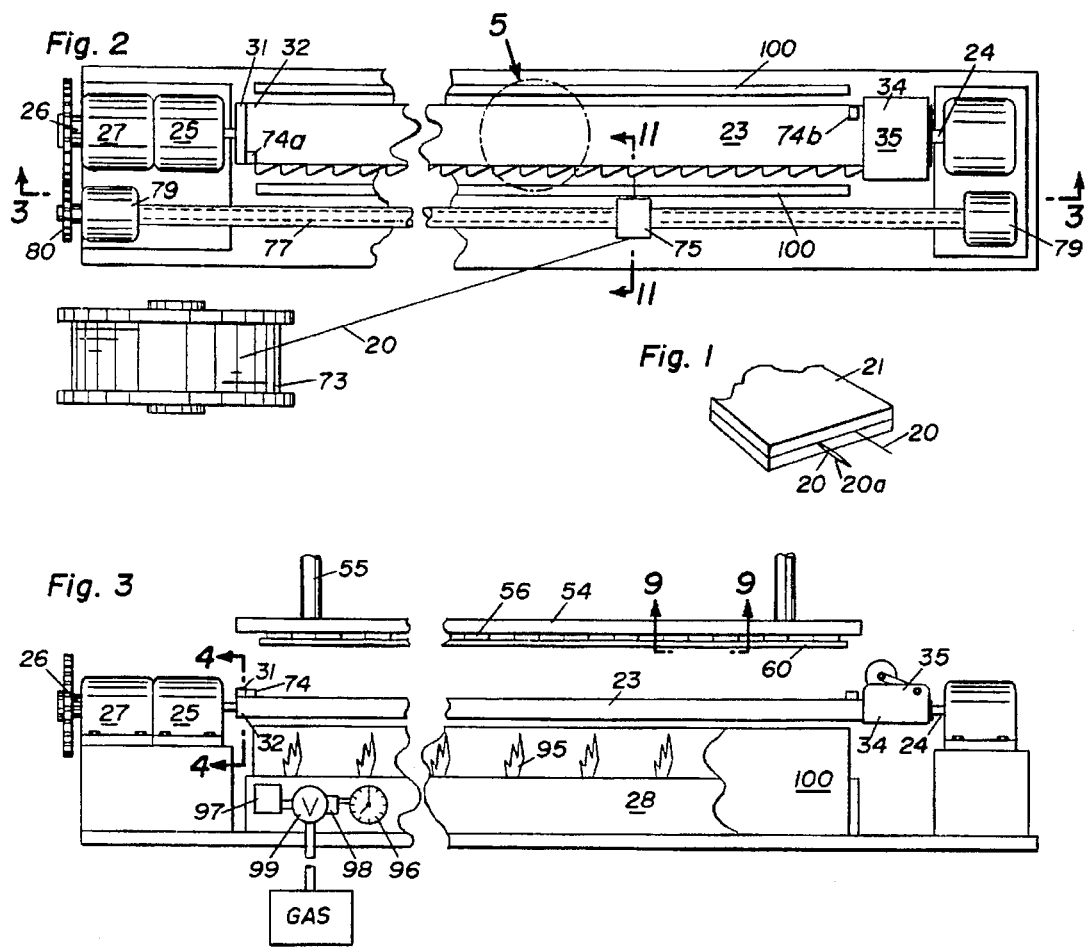
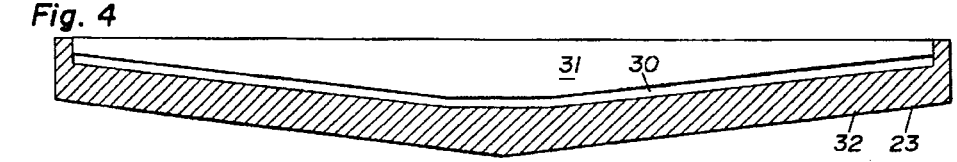
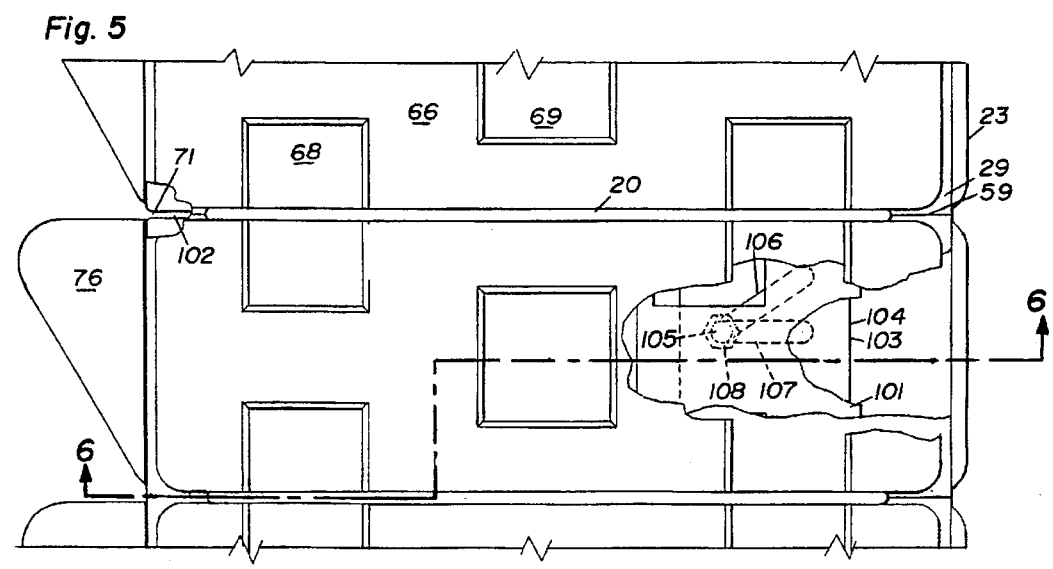

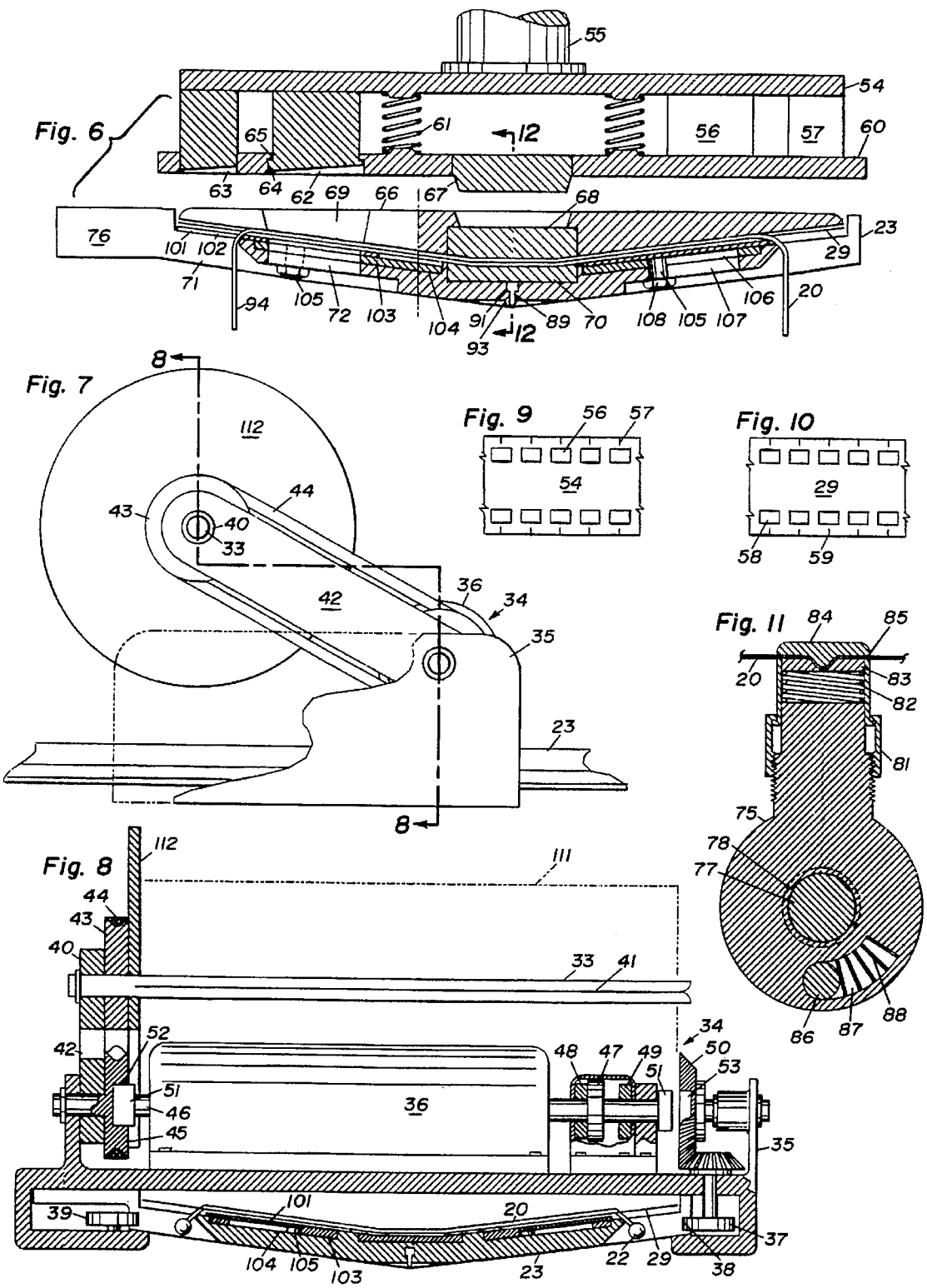

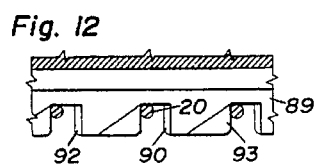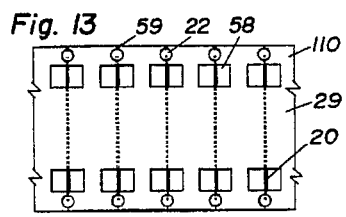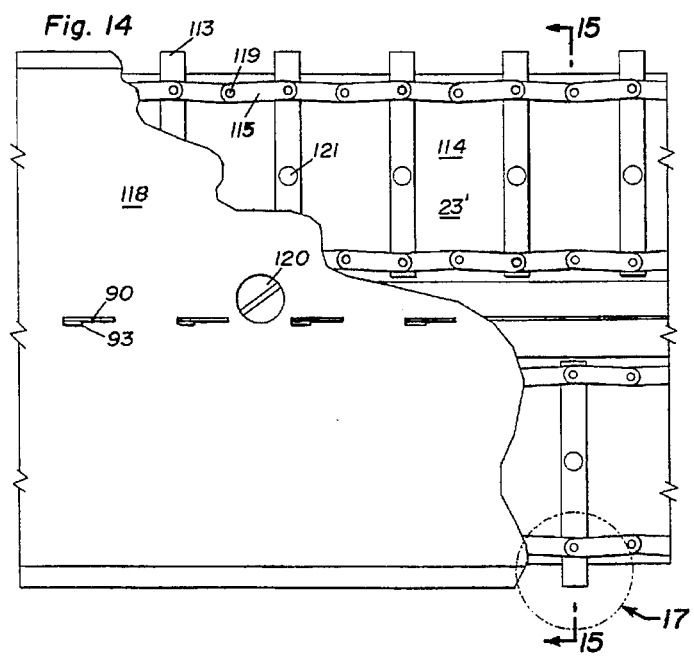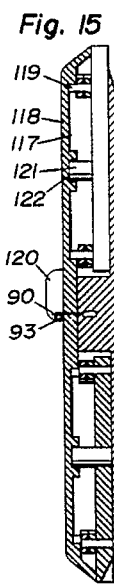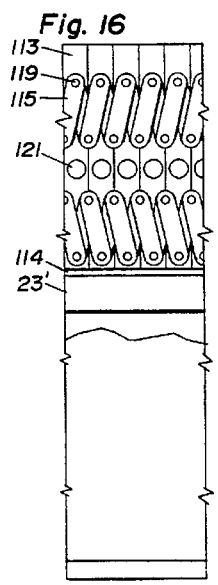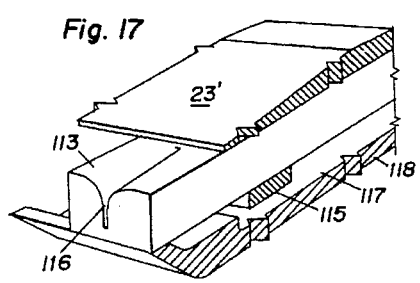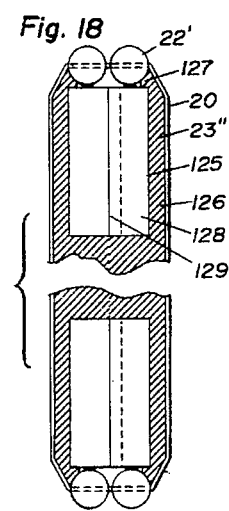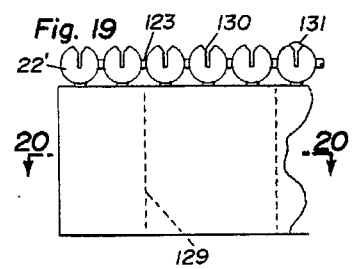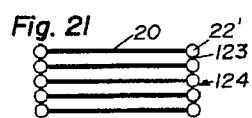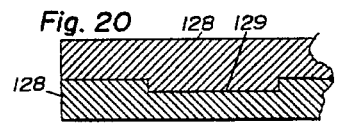

COILABLE STRUCTURES CONTAINING BEADED DENTAL FLOSS AND METHODS AND APPARATUS FOR MAKING THEM

CROSS REFERENCE TO RELATED APPLICATION

This application for patent is related to the following application filed simultaneously herewith: "Apparatus for Using Beaded Dental Floss," Ser. No. 08/519,204, filed Aug. 28, 1995 by Edward E. McCullough and Kevin W. McGaha.

BACKGROUND OF THE INVENTION

1. Field of the Invention

This invention relates to beaded dental floss, especially to coilable structures containing beaded dental-floss segments. More specifically, it pertains to apparatus and methods for forming spherical or spheroidal beads on the ends of dental floss segments by melting the ends of the floss or bonding beads thereto; and for installing the beaded floss segments into coilable structures, whereby a great number of segments can be stored in a small space, easily available to a user.

2. Description of the Prior Art

Dental floss having beads fixed to it for the purpose of easily handling the floss, especially by floss applicators, is known in the prior art.

U.S. Pat. No. 3,843,297 "Apparatus for Preparing Measured Lengths of Dental Floss" to Rene J. Espinosa teaches simultaneously cutting floss and forming "nubs" on the ends of "wax-coated, synthetic, unplasticized, vinyl-resin floss" by protecting portions of the floss from heat and exposing the rest of it to jets of burning gas. As shown in FIG. 6 of that patent, this tends to produce amorphous, roughly disk-shaped nubs on the ends of the floss segments.

U.S. Pat. No. 5,067,503 "Dental Apparatus for Flossing Teeth" to T. W. Stiles teaches molding the end portions of dental floss segments into a plastic card, part of which forms balls of plastic on the ends of the floss. The balls are attached to the rest of the card by fragile connections that can easily be broken, for removal of a floss segment therefrom.

U.S. Pat. No. 4,753,254 to the present inventors teaches pressing preformed beads onto a continuous strand of floss and fixing them with a bonding agent.

U.S. Pat. No. 2,702,555 "Dental Floss Holder" to Michael De Mar teaches fixing the ends of wax-coated dental floss into slots of a disposable floss applicator by melting the ends of the floss so that the wax in the floss flows into the slots to form a bond between the floss and the applicator. The resulting hubs at the ends of the floss segment are necessarily amorphous in order to function best for their intended purposes.

Other patents, known to the present applicants, that teach handling devices (e.g., beads, clamps, molded parts, knots, etc.) attached to dental floss, and associated apparatus for handling such floss, are listed as follows in chronologically-regressive order:

U.S. Pat. No. 5,174,414 to Norman Charatan
U.S. Pat. No. 5,159,943 to John J. Wilson
U.S. Pat. No. 4,986,289 to Charles E. McWhorter
U.S. Pat. No. 4,974,614 to Frank Selker
U.S. Pat. No. 4,898,196 to W. Jeter Eason
U.S. Pat. No. 4,162,687 to Leonard G. Lorch
U.S. Pat. No. 4,016,892 to Ingram S. Chodorow
U.S. Pat. No. 4,006,750 to Ingram S. Chodorow
U.S. Pat. No. 3,974,842 to Ingram S. Chodorow
U.S. Pat. No. 3,631,869 to Rene J. Espinosa
U.S. Pat. No. 3,474,799 to Vito P. Cappello
German Patent No. 1,095,460 to Gustav Frantz
U.S. Pat. No. 1,815,408 to James K. Jordan None of the patents cited above teaches coilable structures that contain segments of dental floss having beaded ends, or how to make such structures; neither do they disclose methods and apparatus for forming spheroidal beads on the ends of floss segments by melting them in a way that avoids the formation of amorphous disks thereon.

SUMMARY OF THE INVENTION

Floss segments having amorphous nubs on their ends are undesirable for use with apparatus contemplated in the present invention; because, in order to function properly, the portions of our apparatus that handle the hubs or beads must conform to fairly precise dimensional tolerances. Hence, it is desirable that the nubs on the ends of the floss segments be spheres or spheroids of a known size. This also avoids tangling of the segments, and spheroids are aesthetically pleasing for commercial purposes. Further, in the experience of the present inventors, balls (of the size used in the present invention) that are molded to the ends of floss segments tend to slip off the floss fairly easily, because of the small area of contact between the molded material and the floss. Hence, making beaded dental floss by melting the floss or by bonding the beads to the floss, as disclosed herein, are more desirable for our purposes.

The present invention teaches a preferred method of forming spheroidal beads by melting the floss. Such beads cannot be pulled off without breaking the floss. Also taught herein is apparatus for press fitting and bonding beads to the floss, so that they also have superior holding properties. In addition, the disclosed apparatus for forming the beaded-floss segments automatically installs them into coilable structures for use with applicator-loading devices.

A primary object of the invention, therefore, is to provide a method and apparatus for making coilable structures that contain segments of beaded dental floss;

Another object of the invention is to provide methods and apparatus for forming spherical or spheroidal beads on thermoplastic dental floss, either on a continuous strand of floss or on the ends of floss segments, by melting the floss in a special way, or by bonding the beads to the floss.

Another object of the invention is to provide a method and apparatus for automatically installing floss segments in coilable structures and for forming spheroidal beads on the ends of the floss in situ.

An important feature of the invention is that it lends itself to high-speed automation of the process of forming beads on floss, installing beaded floss segments in coilable structures, and winding the structures into coils for easy storage and use.

Other objects and advantages of the invention will become apparent as the following detailed description is read with reference to the accompanying drawings. The same numbers refer to the same parts throughout the disclosure.

BRIEF DESCRIPTION OF THE DRAWINGS

In the drawings:

FIG. 1 is a fragmentary perspective view of a clamp/shield holding floss segments for melting;

FIG. 2 is a top view of the apparatus of the invention;

FIG. 3 is a side view of the chassis portion of the apparatus, taken on Line 3—3 of FIG. 2;

FIG. 4 is an enlarged cross section of the chassis taken on Line 4—4 of FIG. 3;

FIG. 5 is an enlarged detail of the portion of FIG. 2 indicated by the phantom circle;

FIG. 6 is a view taken on Line 6—6 of FIG. 5;

FIG. 7 is an enlarged side view of the movable clamp shown in FIG. 3;

FIG. 8 is a section taken on Line 8—8 of FIG. 7;

FIG. 9 is a fragmentary view taken on Line 9—9 of FIG. 3, to show the pattern of knives and punches on the punch bar;

FIG. 10 is a top view of a portion of a tape after having been modified by the knives and punches of FIG. 9;

FIG. 11 is a sectional view of the floss dispenser, taken on Line 11—11 of FIG. 2;

FIG. 12 is a section taken on Line 12—12 of FIG. 6 to show the knives for cutting floss into segments;

FIG. 13 is a fragmentary top view of the paper tape loaded with beaded floss segments;

FIG. 14 is a fragmentary top view of a second embodiment of the chassis of the invention, showing the floss guides in their expanded positions;

FIG. 15 is a cross section taken on Line 15—15 of FIG. 14;

FIG. 16 is similar to FIG. 14, but shows the guides in their collapsed positions;

FIG. 17 is a fragmentary perspective view of the end portion of one of the guides (indicated by the phantom circle in FIG. 14), but rotated 180 degrees about its axis to show the floss-holding slit in the guide);

FIG. 18 is a cross section of a third embodiment of the chassis of the invention;

FIG. 19 is a fragmentary side view of molded bead stock for use in the chassis of FIG. 18;

FIG. 20 is a section taken on Line 20—20 of FIG. 19; and

FIG. 21 is a fragmentary top view of the resulting coilable structure made with the apparatus of FIGS. 14–20.

DESCRIPTION OF THE PREFERRED EMBODIMENTS

The method of making spheroidal beads by melting thermoplastic dental floss essentially comprises: (1) measuring a length of floss that, when melted, will produce a bead of the desired size; (2) exposing that length of floss to heat sufficient to melt it; (3) allowing the spheroid of melting floss to proceed along the floss until it attains the desired size; and (4) stopping its exposure to the heat before the melted spheroid contacts a solid surface (e.g., the surface of a clamp that holds the floss).

If the melted spheroid touches a solid surface, it tends to spread over that surface, turning the spheroid into an amorphous disk shape, which is undesirable for the purposes of this invention. If the heat source is small, it may also be necessary to move either the free end of the floss or the heat source to maintain a distance between them that will insure continued melting of the floss until the desired bead size is produced.

Preventing a melting spheroid of floss from contacting a solid surface can be achieved by any of various means, such as training a tiny laser beam on the floss near the solid surface and closing an electric circuit that will turn off the heat source when the reflected light beam is changed by the presence of the spheroid. However, a preferred method of accomplishing this is simply timing. Given a constant source of heat and a known length of floss to be melted; the required presence of the floss relative to the heat source (for uniform melting of the floss) and the time period necessary to form a spheroid of the desired size, before it contacts the floss-holding device, can be determined and used for automated manufacture of beaded floss. In addition to simply turning off the heat source, exposure of the floss to the heat can be quickly terminated by interposing a shield between the heat source and the melting floss or by quickly increasing the distance between the heat source and floss.

The floss 20 is typically held by some device, represented by a clamp 21 (FIG. 1), that performs the dual functions of holding the floss 20 that is to be exposed to the heat and of shielding the portion of the floss that is not to be melted.

A spheroidal bead 22 can be made on a continuous strand of floss by making an elongated loop 20a of floss, so that its sides are close together (FIG. 1), and by clamping the ends of the loop together, so that, when it is melted, the sides of the loop are joined by a common bead. After the bead has hardened (typically about 0.5 second), the clamp can release the floss. Repeating this operation results in a continuous strand of floss having beads 22 fixed to it. Such beads, however, are not centered on the floss, but are offset to it.

If a single-strand segment of floss 20, having a bead 22 on each of its ends is desired, each end to be melted should preferably be about ½-inch long for the purposes of the present invention. This produces spheroidal beads 22 that are slightly less than 1/16-inch in diameter, if nylon floss is used that is commonly sold under the label "extra fine."

A preferred apparatus of the invention (FIGS. 2 and 3) for making coilable structures that contain such beaded floss segments has an elongated chassis 23 with a short shaft 24 fixed to each end and journaled in a bearing 25; so that the chassis can be rotated about its longitudinal axis. At one end, the shaft 24 extends through its bearing 25 and is fastened to the shaft 26 of an electric motor 27 (the chassis motor) by a conventional coupling 28, for rotation of the chassis 23.

In a preferred embodiment of the invention (FIGS. 2–13), a flexible floss support, preferably a paper tape 29, is threaded through a shallow, V-shaped opening 30 in a guide 31 (FIGS. 2,3, and 4) on the forward end 32 of the chassis 23. It is then inserted into the longitudinal slit 41 in the retaining shaft 33 of a movable clamp 34. By this means, the tape 29 is guided along the surface of the chassis and bent into the form of a shallow "V" shape in conformity therewith.

The movable clamp 34 (FIGS. 2, 3, 7 and 8) has a carriage 35 powered by an electric motor 36 (the clamp motor) that rotates a rubber wheel 37, fastened to the carriage and engaging a groove 38 in a side of the chassis 23. Three idle wheels 39, also attached to the carriage, provide stability. One wheel 39, attached to the carriage 35 in tandem with the powered wheel 37, engages the same groove as that wheel, while the other two wheels 39 engage a similar groove 38 on the opposite side of the chassis.

The essence of the movable clamp 34 is a retaining shaft 33, held at one end by a bearing 40 and free at its other end. The tape 29 is inserted into a long slit 41 in the shaft and secured therein by a rotation or two of the shaft. The bearing 40 that holds the shaft 33 is pivotally attached to one end portion of a link 42. The other end of this link is pivotally attached to the carriage 35, so that the link can freely swing in a vertical plane parallel to the chassis. The retaining shaft 33 has a first pulley 43 fixed to it that can be rotated by a belt 44. This belt also passes over a second pulley 45 that is positioned to be engageable by the motor shaft 46.

A clutch plate 47, made of ferrous material and fixed to the motor shaft 46, can engage either the pulley 45 or the gear 50 when the electromagnet 48 or 49, respectively, is energized to attract the clutch plate and move the motor shaft longitudinally (FIG. 8). A key 51 on the left-hand end of the motor shaft 46 (as shown in the Figure) can engage a slot 52 in the pulley 45 This slot 52 has the same shape as the cross section of the key, so that the pulley is rotated when the electromagnet 48 is energized. A similar key 51 on the right-hand end of the shaft 46 engages a similar slot 53 in the gear 50, when the electromagnet 49 is energized.

A punch bar 54 (FIGS. 3 and 6), having about the same length as the chassis 23, is suspended directly above the chassis by hydraulic actuators 55. The under side of the punch bar 54 is equipped with punches 56 and knives 57 (FIGS. 6 and 9) that can produce the pattern of holes 58 and slits 59 in the tape 29 shown in FIG. 10. A shield 60 in the form of a flat plate is spaced below the punch bar 54 by compression springs 61. This shield has holes 62 and slots 63 through which the punches 56 and knives 57 can extend. In its normal position, the under surface of the shield 60 extends slightly below the tips of the knives and punches, as a safety feature. The punches 56 are narrowed slightly to provide shoulders 64, against which flanges 65, in their corresponding holes 62 in the shield, can bear for retention of the shield 60 to the punch bar 54.

The under side of the shield 60 carries a series of holding plates 66 (FIGS. 5 and 6), temporarily attached to it by electromagnets 67 in the shield 60 that, when energized, attract bodies of ferrous material 68 in the plates 66. The holding plates can be deposited on the tape, to hold it against the chassis in the manner of paper weights, and the punches 56 and knives 57 can create the cited pattern of holes and slits in the paper tape in one operation: (1) The punch bar 54 is lowered until the holding plates 66 contact the tape and chassis, and the electromagnets 67 are de-energized; ferrous bodies 68 in the holding plates 66 are then attracted to permanent magnets 70 in the chassis, so that the tape is clamped securely between the holding plates and the chassis. (2) Further lowering of the punch bar causes the punches 56 to extend through holes 69 in the holding plates 66 and the knives 57 to extend between plates. (3) With still further lowering, the punches and knives pass through the tape and through matching rectangular holes 72 and slots 71 in the chassis 23 to create the cited pattern of holes and slits in the tape. The holes 72 in the chassis act as punch dies to cooperate with the punches 56 to make precise, rectangular holes 58 in the tape.

After this is completed, the punch bar 54 is lifted high enough above the chassis 23 that the chassis can be rotated about its axis beneath the punch bar. During this rotation, the holding plates 66 remain in position to clamp the tape 29 against the chassis 23. The end of a long strand of dental floss 20, from a floss-supply reel 73 is then inserted into a spring clamp 74a in the lower right-hand corner of the chassis (as shown in FIG. 2). Then, beginning at the forward end of the chassis, the floss dispenser 75 moves aftwardly the distance between two adjacent slits 59 in the sides of the tape 29 as the chassis completes one clockwise rotation as seen from its forward end). Triangular cams 76 on one side of the chassis 23 guide the floss 20, as the chassis rotates, to create diagonal wrappings of floss on the under side of the chassis 23 and wrappings perpendicular to the tape 29 on the upper side. The cams 76 and slots 71 also guide the floss so that it enters deeply into the slits 59 in the paper tape. When the floss has been completely wrapped on the chassis and tape, the free end of the floss 20 is severed from the floss supply 73 by conventional means not shown, and secured beneath a second spring clamp 74b.

The floss dispenser 75 (FIGS. 2 and 11) is essentially a spring clamp for providing a constant, adjustable tension on the floss. Its motion is synchronized with the rotations of the chassis, as described above, by a long screw 77 that passes through a threaded hole 78 in the dispenser. The screw 77 is journaled at its ends in bearings 79, so that it is essentially parallel to the chassis 23. The screw 77 and the chassis 23 are connected at their forward ends by gears 80 that transmit rotary motion, in the desired ratio, from the motor 27 (and chassis 23) to the long screw 77, to produce the relative motions of the chassis and the floss dispenser described above. Pulleys, not shown, could also be used to accomplish this purpose, provided by the gears, as could friction wheels. Tension on the floss can be adjusted by rotating a threaded coupling 81 that regulates the force exerted by a compression spring 82 on a disk 83. This disk confines the floss 20 against the inside of a cap 84 as it passes through the cap via two holes 85. Rotation of the dispenser 75 about the long screw 77, as the screw turns, is limited by a rod 86 that passes through an opening 87 in the dispenser 75 and is fixed at its ends to the bearings 79. The opening 87 is arcuate in form, concentric about the long screw 77, and has a compression spring 88 confined between one end of it and the rod 86. This permits the floss dispenser 75 to lean toward the chassis 23 and return to an upright position, to maintain a fairly constant tension on the floss 20, as it moves over the triangular cams 76.

An elongated blade 89 (FIGS. 6 and 12), having a series of knives 90 on it (one for each wrapping of floss on the underside of the chassis 23) similar to the teeth of a saw blade, is seated, for longitudinal sliding motion, in a groove 91 in the center of the under side of the chassis 23. To cut the floss into segments, this blade 89 is moved longitudinally, either manually or by some conventional mechanism (not shown), such as an electromagnet operating against a compression spring. The cutting edge 92 of each knife 90 is adjacent a floss wrapping on the under side of the chassis 23, and slides against a protuberance 93 on the inside of the groove 91 for a scissors action on the floss 20.

The cut ends 94 of the floss (FIG. 6) are then exposed to heat from a heat source 95 (FIG. 3) that is sufficiently hot to melt them (of the order of 470 degrees Fahrenheit, for nylon floss). This source of heat 95 could be any of several clean sources, such as an electric heater or heated air. However, a preferred source is a burner for burning a flammable gas (e.g. natural gas). The melting typically starts on the end of each floss segment, where it forms a transparent spheroid 22 that progresses along the floss. If permitted to contact a solid surface, the spheroids tend to flatten against that surface to become amorphous disks, as noted above. Hence, the melting is stopped before the spheroids 22 reach the chassis surface. This could be accomplished by any of the methods noted above, or by introducing cold air that seeps out from between the chassis and tape or holding plates. However, in a preferred embodiment of the invention, this is done by timing the melting process, using any of a number of well-known timing devices, represented by a clock 96 (FIG. 3). The timing device turns the gas jets off via a conventional switch 97, solenoid 98 and valve 99 when the given time has elapsed that allows the spheroids 22 to approach within about $\frac{1}{32}$-inch of the chassis surface.

Two elongated heat shields 100, one on each side of the gas jets, perform the dual purpose of preventing the jets from igniting clothing, etc., and of providing a uniform temperature environment beneath the chassis 23; so that moving the jets or the cut floss ends to maintain a specified distance between them is unnecessary.

A second set of elongated shields 101 (FIGS. 5, 6 and 8), of thin, heat-resistant material (preferably sheet steel), substantially the same length as the chassis 23, are interposed between it and the tape 29. Their purpose is to protect the paper tape from the heat. They also function as a means for temporarily retaining the floss segments on the chassis and tape, before the ends of the floss are melted. For maximum protection of the tape 29, these shields 101 have thin slits 102 coincident with the wider slots 71 in the chassis. These slits 102 in the shields 101 are wide enough to permit passage of the floss 20, but not of the spheroids or beads 22. Hence, the shields 101 must be withdrawn from the edges of the tape 29 after formation of the beads 22; so that the tape, loaded with beaded floss, can be removed from the chassis 23. This withdrawal of the shields 101 is accomplished by an elongated actuating plate 103, seated in a long channel 104 in the upper surface of the chassis 23, under each shield 101. Short pins 105, extending downwardly from the underside of each shield, engage diagonal slots 106 in the plate 103; so that, when these plates are moved longitudinally, the shields 101 are moved inwardly or outwardly, relative to the longitudinal axis of the chassis 23. Motion of the shields 101 is maintained at right angles to the axis of the chassis by slots 107 in the underside of the chassis 23, through which the pins 105 also extend. Nuts 108, engaging threaded end portions 109 of the pins 105, retain the shields 101 and their actuating plates 103 on the chassis 23.

When the loaded tape 110 (FIG. 13) is ready to be removed from the chassis 23, the shields 101 are withdrawn toward the center of the chassis 23, and the punch bar 54 is lowered so that the punch shield 60 just contacts the tape 29 (further lowering would cause the punches to damage the beaded floss segments). The electromagnets 67 are then energized to lift the holding plates 66 from the chassis 23. The clutch 47 on the movable clamp 34 then engages the pulley 45, the direction of the motor 36 is reversed, and it is energized to rotate the pulley 43 on the retaining shaft 33. In this way, the tape is wound into a coil on the shaft 33, with the mass of the carriage providing about two ounces of tension on the tape, as the carriage moves forwardly on the chassis.

Until the tape 29 is wound, it is slightly "V"-shaped in cross section (FIGS. 6 and 8). Hence, winding the tape 29 into a coil straightens it transversely, thereby taking up the slack in the floss that results from the fact that the bead formation stops at about 1/32-in. from the surface of the tape. The beads 22 then lie snugly at the ends of their respective slits 59 in the paper tape 29 for secure retention.

When the loaded tape 110 has been rolled into a coil 111 (Represented by phantom lines in FIG. 8), a movable disk 112 at the pulley end of the retaining shaft 33 is slid along the shaft, either manually or by other conventional means, to push the coil of tape off the shaft and into a cartridge, not shown.

A second embodiment of the invention is shown in FIGS. 14–17. As in the embodiment described above, the apparatus of the invention has an elongated chassis 23' rotatable about its longitudinal axis by an electric motor 27 in the manner described above.

However, in this embodiment, the punch bar 54, with its hydraulic actuators, punch dies, and holding plates, is eliminated. Also, the chassis 23' is flat. An array of sliding guides 113 is confined in a first channel 114 in each edge of the chassis 23'. Each guide 113 is fastened to an adjacent guide by two pairs of toggle links 115. The width of each guide 113 is about the same as the desired diameter for a bead 22, and each has a flared slit 116 in its outer end for easy insertion of floss 20 (FIG. 17). The entire array of guides 113 in each edge of the chassis 23' can be expanded to a predetermined length, with uniform spacing between the guides, by moving a guide on one end of the array outwardly along the axis of the chassis 23'. The array of guides 113 can also be collapsed into the position shown in FIG. 16 by moving the same end of the array in the opposite direction. Expansion and collapse of the arrays of guides 113 is accomplished either manually or by some other conventional means, such as by attaching a continuous cable (not shown) to one of the guides, stretching the cable over two pulleys so that the cable is parallel to the chassis, and rotating one of the pulleys with an electric motor. The end guide 113 that is not being moved to expand or collapse the array is fastened to the chassis. Over-the-center movement of the toggle links 115 is prevented by the width of a second channel 117, for each array, in the chassis cover 118, into which the pins 119 that join the links of each pair, extend. The chassis cover 118, having approximately the same dimensions as the chassis 23', is fastened to the chassis by screws 120 that engage threaded holes in the chassis, and forms one side of each channel 114. Pins 121, fixed to the central portions of the guides 113, extend into third channels 122, formed in the chassis cover 118, to retain the guides 113 in the chassis.

In operation, this embodiment of the invention functions similarly to that of the embodiment described above. The arrays of guides are expanded, the dental floss is wrapped onto the chassis (into the slits 116 in the guides), using a clamp 74 and a floss dispenser 75 in the same way as described above. Also, as described, the floss 20 is cut into sections, using the long blade 89 with multiple knives 90 thereon. Then, as described, the cut ends of the floss are exposed to the same kind of heat source, and timed by the same timing means until the proper beads have formed thereon. The arrays of guides 113 are expanded for this operation to avoid the possibility that the melting beads on adjacent floss segments may join to form a single bead.

The arrays of guides 113 are then collapsed and each row of beads is covered with a thin stream of liquid adhesive material, sufficient to join adjacent beads together with a short neck or isthmus 123. This material is preferably quick setting, nontoxic, and flexible enough when dry to permit rolling the resulting, floss-segment tape 124 (FIG. 21) into a coil. A preferred material for this purpose is latex, although any other nontoxic material having these characteristics could serve this purpose. When the bond has set, the resulting tape-like structure 124 is rolled into a coil for use in other apparatus.

A third embodiment of the invention (FIGS. 18–20), also eliminates the hydraulically-operated punch bar 54 and the holding plates 6. The chassis 23" of this embodiment is a flat, elongated bar, similar to the chassis 23' described above; and, similarly, it has a channel 125 in each of its edges. The outwardly-extending, parallel members or sides 126 of each channel 125 have short, inwardly-extending flanges 127 for retaining a pair of long bars 128 that can be slid endwise into the channels 125. The bars 128 are preferably of molded, thermoplastic material having beads 22' molded to them (FIGS. 18 and 19). Each bead 22' is joined to the adjacent bead with a small, flexible neck or isthmus 123. As viewed from their ends (FIG. 18), the bars 128 are mirror images of one another, formed to fit the channels 125 as a pair. They have transverse tongue-in-groove joints 129, so that, when fitted together (FIGS. 18 and 20), the bars 128 are in longitudinal registry and the transverse, flared slits 130 in the beads 22' of one bar 128 are precisely aligned with those of the other.

As in the two embodiments described above, floss 20 is supplied via a dispensing mechanism 75 that also provides tension on the floss. And as in those embodiments, the chassis 23" is rotated about its axis, by the same kind of equipment, while the floss 20 is wound—this time into the slits 130 in the beads 22'. Beads 22' held in opposite edges of the chassis are staggered, longitudinally (as are the guides 113 of the second embodiment), so that the long screw 77 (and the floss dispenser 75) can move at a constant speed without interruption until the winding is complete. The winding tension is such that the floss 22 is press-fitted into the slits 130 of the beads 22'. Each slit 130 extends into its bead 22' by slightly more than the bead's radius, so that the floss 20 is positioned in the center of each bead 22'.

After the winding has been completed, each bead 22' is fixed permanently on the floss 20 with a drop of liquid adhesive 131 (shown on the right-end bead of FIG. 19). Although other adhesives could be used, a preferred adhesive is a cyanoacrylate-containing resin, sold under the trademark "Krazy Glue," by Krazy Glue, Inc. of Itasca, Ill. A knife (not shown) is then passed longitudinally along each edge of the chassis 23", severing the floss connections between beads of adjacent rows, so that the two plastic bars 128 in each channel 125 are separated. The pairs of bars 128 are then removed from the chassis 23" and the rows of beads 22' are sheared from their respective bars 128. This leaves two long tape-like structures (like that shown in FIG. 21) comprising parallel segments of floss 20, each having a bead 22' on each of its ends, and each bead being connected to a bead of the adjacent floss segment by a neck or isthmus 123; and two long bars of plastic that can be recycled. Each edge of the coilable structure 124 is formed by a row of beads 22'. The resulting, structures 124 can then be wound into coils for use in other equipment.

Although in a preferred form of this embodiment of the invention, as described above, one row of beads 22' is molded to one bar 128, and these bars are used in a side-by-side arrangement, it is possible that two rows of beads could be molded adjacent one another on the same bar. In this case, the means for shearing the beads from the bar could be a knife having the cross-sectional form of an inverted "T"; so that, moving from one end of the bar to the other, the two rows of beads could be separated from each other and also from the bar simultaneously. Also, it may be thought desirable to place the beads of adjacent rows at a slight angle to the perpendicular, to compensate for the steady movement of the floss dispenser parallel to the chassis 23". However, the flared openings on the slits 130 can be made to compensate adequately for this motion, if the beads are in a side-by-side arrangement.

Also, it should be noted that coilable structures containing segments of beaded dental floss could be made if only one bar 128, having one row of beads thereon, were to be installed in each channel 125. However, if this were done, the floss wrappings on one side of the chassis 23" would have to be separated from the rows of beads. Hence, this would be wasteful of floss, and would be less efficient than using two bars 128 in each channel 125, as described.

Although the invention embodiments have been described specifically with regard to detail, it should be noted that details can be modified without departing from the spirit and scope of the invention, as it is defined in the following claims. For example, although the beads on the floss segments of the coilable structures have been described as being preferably spherical or spheroidal, it is conceivable that the coilable structures may be useful in apparatus wherein beads of other shapes can be used.

The invention claimed is:

1. Apparatus for making a coilable structure containing parallel segments of dental floss, wherein each segment has a bead fixed to each of its ends, comprising:
    an elongated chassis;
    means for winding dental floss, in a controlled manner, onto the chassis;
    means for dividing the wound floss into segments;
    means for temporarily holding the segments on the chassis;
    means for fixing beads onto the ends of each floss segment; and;
    means for attaching the floss segments into an elongated, coilable structure.

2. The apparatus of claim 1 wherein the means for winding dental floss, in a controlled manner, on the chassis comprises: a means for rotating the chassis about its central, longitudinal axis; and means for dispensing floss that creates a desired pattern of wound floss on the chassis.

3. The apparatus of claim 2 wherein the means for rotating the chassis comprises: a shaft fixed to each end of the chassis; bearing means for supporting the shafts; and a motor operatively attached to one of the shafts.

4. The apparatus of claim 2 wherein the means for dispensing floss comprises an adjustable-pressure, spring clamp, through which the floss passes, for providing tension on the floss being dispensed to the chassis as it is rotated; and means for moving the spring clamp relative to the chassis in a controlled manner, so that the spacings of floss windings on the chassis are arranged as desired.

5. The apparatus of claim 4 wherein the means for moving the spring clamp relative to the chassis in a controlled manner comprises: a long screw that engages a threaded hole defined in the spring clamp; bearings for supporting the screw relative to the chassis; means for limiting the angle through which the spring clamp can rotate about the long screw; and means for connecting the long screw to the chassis for rotational velocity of the screw proportional to that of the chassis.

6. The apparatus of claim 5 wherein the means for limiting the angle through which the spring clamp can rotate comprises: a compression spring seated in a arcuate aperture defined in the spring clamp, concentric about the long screw; a long rod, substantially the same length as the long screw, that passes through the arcuate aperture so that the compression spring bears against it; and support means for supporting the long rod parallel to the long screw.

7. The apparatus of claim 5 wherein the means for connecting the long screw to the chassis for rotation of the screw proportional to the rotation of the chassis comprises: at least one gear fixed to one end of the long screw; and at least one gear attached to the adjacent end of the chassis shaft, said gears sized and meshed to create the desired rotational velocity of the long screw, relative to that of the chassis.

8. The apparatus of claim 2 wherein the chassis defines narrow slits in its edges, perpendicular to its axis (to comprise the means for temporarily holding the floss segments to the chassis), and wherein the means for dispensing floss to create a desired pattern of wound floss on the chassis includes a series of cams fixed to an edge of the chassis to guide the floss into the slits, whereby the pattern of wound floss on the chassis comprises wrappings that are perpendicular to the axis of the chassis on one side thereof and diagonal on the other side.

9. The apparatus of claim 1 wherein the chassis defines a long groove in one side thereof, and the means for dividing the floss into segments comprises a long blade, seated in the groove for longitudinal sliding motion, and at least one knife fixed to said blade and extending outwardly sufficient to cut the windings of floss on the chassis.

10. The apparatus of claim 1 wherein the means for attaching the floss segments into a coilable structure comprises:

a flexible tape; and means for mounting the floss segments onto the tape.

11. The apparatus of claim 10 further including bodies of ferrous material; and permanent magnets fixed to the chassis and positioned to attract said bodies, so that the tape is confined between then and the chassis, for retaining the tape to the chassis as it rotates.

12. The apparatus of claim 10 further including knives for making slits in the edges of the tape, coincident with slots defined in the edge portions of the chassis, so that the floss is wound into the slits in the tape, as the means for mounting the floss segments onto the tape; means for supporting the knives; and means for moving them to cut the tape.

13. The apparatus of claim 11 wherein the means for supporting the knives comprises an elongated bar, to which they are attached; and the means for moving the knives to cut the tape comprises hydraulic actuators, each operatively stationary at one end, and attached at its other end to the bar to support it substantially parallel to the chassis.

14. The apparatus of claim 13 including means attached to said bar for temporarily retaining the ferrous bodies, when they are not being used for holding the tape to the chassis.

15. The apparatus of claim 14 wherein the means for retaining the ferrous bodies comprises electromagnets fixed to said bar, the electromagnets being more powerful than the permanent magnets on the chassis, so that, when energized, the electromagnets can lift the ferrous bodies off the chassis and retain them.

16. The apparatus of claim 1 wherein the means for fixing beads to the end portions of the floss segments comprises: a source of heat sufficient to melt the floss; means for shielding the central portion of each floss segment from exposure to heat; and means for limiting exposure of the end portions of the floss segment to said heat, so that spheroids of melted floss thereon are prevented from contacting a solid surface before solidifying.

17. The apparatus of claim 16 wherein the means for attaching the floss segments into a coilable structure comprises a flexible tape; the means for shielding the central portions of the floss segments from said heat comprises the chassis; and the means for limiting exposure of the end portions of the floss segments to heat from the heat source comprises: a timer for measuring the time period that elapses between initial exposure of the floss to the heat and when a melted spheroid, traveling on the floss, has developed to the desired size and is free of contact with a solid surface; and means responsive to the timer for terminating exposure of the floss to the heat source when said time period has elapsed.

18. The apparatus of claim 17 wherein the heat source comprises a burner for burning flammable gas; and further includes: a source of flammable gas connected to the burner for flow of gas thereto; and wherein the means for terminating exposure of the floss to heat from the heat source comprises a solenoid-operated valve positioned to control the flow of flammable gas from its source to said burner; and means for operating said valve in response to the timer, so that the flow of gas to the burner is stopped when said time period has elapsed.

19. The apparatus of claim 16 wherein the means for joining the floss segments into a coilable structure comprises a flexible tape, defining slits in its outer edges as a means for retaining floss segments thereto, said tape temporarily held on the chassis while it is wound with the floss; further including a thin, elongated, heat-resistant shield defining slits in its outer edge, coincident with those of the tape, so that floss is wound into its slits and those of the tape simultaneously, said shield being fastened to the chassis for inward and outward movement relative to the axis thereof, and normally positioned so that it protects the tape from said heat source, but movable toward the center of the chassis for release of the floss after beads have formed thereon.

20. The apparatus of claim 1 wherein the means for temporarily retaining the floss segments onto the chassis comprises: an array of parallel guides, substantially perpendicular to the axis of the chassis, each guide defining a slit in its outer-end portion, into which a floss winding can be press-fitted; means for fastening the guides together so that the array can be collapsed and expanded with constant distances between the guides; and means for retaining each array to the chassis for sliding motion thereon.

21. The apparatus of claim 20 wherein the means for fastening the guides together comprises at least one set of toggle links between each two adjacent guides, each outer end of each set of links being fastened, for pivotal motion, to a guide, and wherein the chassis defines a first channel in each of its longitudinal edges, in which each array of guides is seated; and further defines a long, third channel in one side of each first channel, parallel to the edge of the chassis, wherein the means for retaining each array of guides in the chassis comprises a short pin fixed to each guide so that it extends into said third channel.

22. The apparatus of claim 1 wherein the means for fastening the beaded segments of floss together into a coilable structure comprises an adhesive that connects adjacent beads on the end portions of each segment of floss together, to form a tape with a row of beads defining each edge thereof.

23. The apparatus of claim 1 wherein the chassis defines a channel in each of its longitudinal edges and wherein the means for fixing beads to the end portions of the floss segments comprises: a bead stock comprising an elongated bar and a series of beads fixed to the bar in tandem arrangement, each bead being connected directly to each adjacent bead, and each bead defining a slit in its outer portion, substantially perpendicular to the bar, so that windings of floss can be press-fitted into the slits when at least one bar is fitted into each channel.

24. The apparatus of claim 23 wherein two of said bars are fitted in a side-by-side relationship in each channel, so that their beads are aligned as desired to create two coilable structures simultaneously, one on each side of the chassis, when floss is wound on the chassis and press-fitted into the beads.

25. The apparatus of claim 24 wherein the interface surfaces of two adjacent bars are shaped to prevent longitudinal displacement of one bar relative to the other, when the two bars are fitted together and installed in one of said channels in the chassis, so that adjacent beads on the two bars are automatically aligned as desired.

26. The apparatus of claim 23 wherein the beads in one channel are staggered, in their longitudinal spacings, relative to those in the other channel of the chassis, so that a constant-velocity movement of a floss dispenser, parallel to the chassis, results in precision winding of the floss into the slits in the beads.

27. The apparatus of claim 23 further including a bonding agent applied to each bead, after it has been press-fitted onto the floss, for fixing the bead thereto.

* * * * *